United States Patent
Glaser-Seidnitzer et al.

(10) Patent No.: US 8,838,506 B2
(45) Date of Patent: Sep. 16, 2014

(54) METHOD TO CONFIGURE AN IMAGING DEVICE

(75) Inventors: Karlheinz Glaser-Seidnitzer, Fuerth (DE); Werner Hauptmann, Hoehenkirchen (DE); Berthold Kiefer, Erlangen (DE); Clemens Otte, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 406 days.

(21) Appl. No.: 13/207,564

(22) Filed: Aug. 11, 2011

(65) Prior Publication Data

US 2012/0041909 A1    Feb. 16, 2012

(30) Foreign Application Priority Data

Aug. 16, 2010   (DE) .......................... 10 2010 034 430

(51) Int. Cl.
*G06F 15/18* (2006.01)
*G06F 19/00* (2011.01)
*G01R 33/54* (2006.01)

(52) U.S. Cl.
CPC ............ *G06F 19/325* (2013.01); *G01R 33/546* (2013.01); *G01R 33/543* (2013.01)
USPC .......................................................... 706/12

(58) Field of Classification Search
CPC ..... G06F 15/18; G06F 19/325; G01R 33/543; G01R 33/546
USPC .......................................................... 706/12
See application file for complete search history.

(56) References Cited

U.S. PATENT DOCUMENTS

| | | | | |
|---|---|---|---|---|
| 6,101,407 | A * | 8/2000 | Groezinger | 600/407 |
| 6,287,257 | B1 * | 9/2001 | Matichuk | 600/437 |
| 6,412,980 | B1 * | 7/2002 | Lounsberry et al. | 378/207 |
| 6,473,659 | B1 * | 10/2002 | Shah et al. | 700/79 |
| 6,760,755 | B1 * | 7/2004 | Brackett | 709/214 |
| 7,542,792 | B2 * | 6/2009 | Wollenweber et al. | 600/407 |
| 2005/0121505 | A1 * | 6/2005 | Metz et al. | 235/375 |
| 2005/0197864 | A1 * | 9/2005 | Koritzinsky et al. | 705/2 |
| 2007/0211756 | A1 * | 9/2007 | Glaser-Seidnitzer et al. | 370/466 |
| 2008/0309783 | A1 * | 12/2008 | Nozaki | 348/222.1 |
| 2009/0161827 | A1 * | 6/2009 | Gertner et al. | 378/65 |
| 2009/0276392 | A1 * | 11/2009 | Yan | 706/60 |
| 2010/0080427 | A1 * | 4/2010 | Yeluri et al. | 382/128 |
| 2010/0138523 | A1 * | 6/2010 | Urness et al. | 709/222 |
| 2011/0206250 | A1 * | 8/2011 | McGinnis et al. | 382/128 |

FOREIGN PATENT DOCUMENTS

DE      198 28 528 A1    12/1998

* cited by examiner

*Primary Examiner* — Jeffrey A Gaffin
*Assistant Examiner* — Dave Misir
(74) *Attorney, Agent, or Firm* — Schiff Hardin LLP

(57) ABSTRACT

A database contains variants of protocols for the operation of magnetic resonance tomographs as well as different types of magnetic resonance tomographs. Each variant contains parameter values and is associated with one of the types. In a training phase, relationships are determined between the parameters among one another and/or between the parameters and the associated types and are stored as patterns in a knowledge base. A protocol plan for the operation of a new magnetic resonance tomograph is created later in an application phase using the determined pattern. The method offers the advantage that the efficiency and quality of the automatic conversion of the protocols is improved. The improved quality of the protocol plan reduces operating time and costs for a manual post-processing of the protocols. Furthermore, a higher consistency of the protocols among one another is achieved both between product families and between individual configurations.

9 Claims, 6 Drawing Sheets

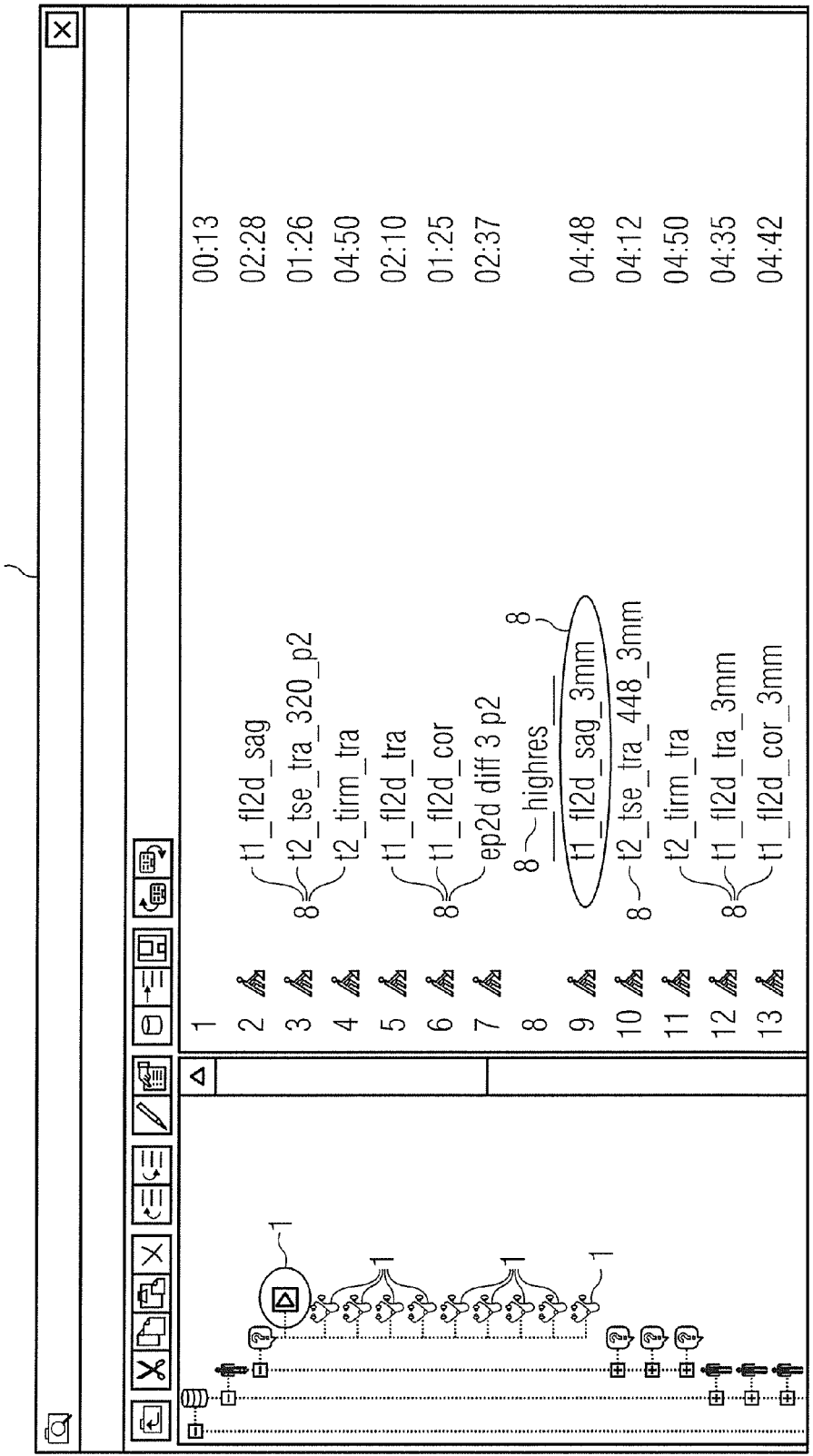

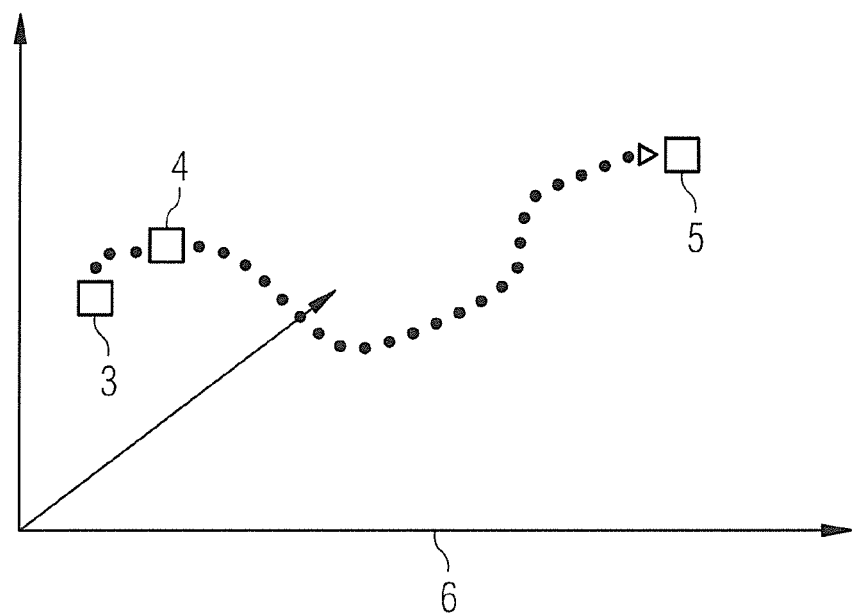
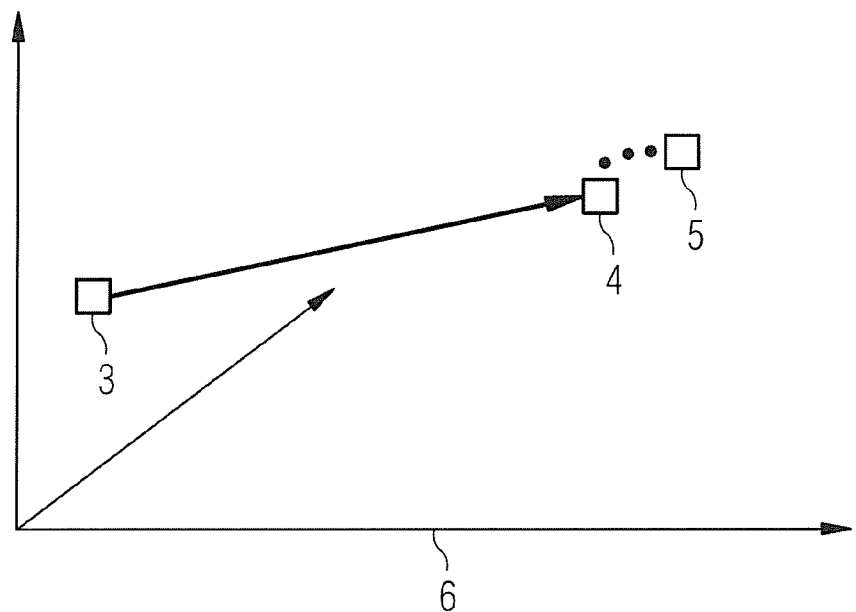

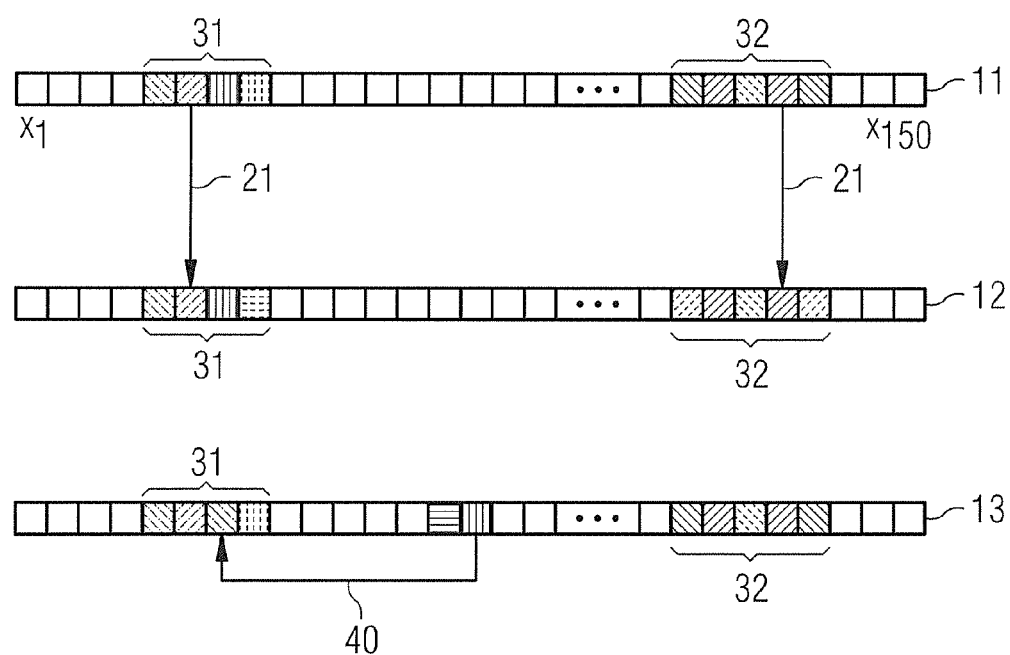

METHOD TO CONFIGURE AN IMAGING DEVICE

BACKGROUND OF THE INVENTION

1. Field of the Invention

The present invention concerns a method for configuring an imaging device, as well as a computer programmed to implement such a method, and a non-transitory computer-readable storage medium encoded with programming instructions that cause a computer to implement such a method, when the storage medium is loaded into the computer.

2. Description of the Prior Art

Different imaging devices—for example magnetic resonance tomography systems, computed tomography systems, ultrasound apparatuses and x-ray systems—are known from medical technology. In order to achieve an uncomplicated use of these complex systems, it is necessary to configure the imaging devices. A number of measurement instructions and other settings that are specific to the respective imaging device (but possibly also to a specific use case) must be established for this purpose. The cited imaging devices require complex and extensive settings in order to acquire images in a desired quality or with desired properties with regard to resolution, contrast, section, size, etc.

The measurement instructions and settings that are required for a medical examination with the imaging device typically are stored in protocols. The protocols contain all necessary information in order to operate the imaging device so that the medical examination can be implemented. The protocols are typically tailored specifically to the properties of a specific imaging device. In the event that the imaging device can be operated with different software systems, the protocols are additionally tailored to the respective software system.

In a magnetic resonance tomography system, each protocol describes a sequence for image acquisition, typically with a duration of a few minutes. A sequential execution of multiple protocols or sequences is designated as a program. 1500 to 1800 protocols typically exist for the operation of a magnetic resonance tomography system. The number of protocols and programs is thus very extensive.

For example, each protocol may contain approximately 150 parameters that define the technical process of the image acquisition. The term "parameters" means properties, measurement instructions or other settings for the imaging device or its software as well as other work steps within the scope of the operation of the imaging device or the preparation and implementation of a medical examination. These can also be other settings that again require additional steps and/or substeps. For example, the parameters are contrast agent information or other configurable settings of the imaging device, for example an echo time, acquisition time, resolution, bandwidth, turbo factor, dimensions of field of view, slice count, slice thickness, etc.

The parameter values of these parameters depend on the type of the respective imaging device. The type is defined by a number of attributes that describe predetermined properties of the imaging device. In the example of a magnetic resonance tomography system, these properties are its field strength, its gradient system, or the number of its coils, for instance.

In order to convert an existing protocol for the operation of a magnetic resonance tomography system of a new type, up to 25 parameter values must be adapted in the protocol. Due to the high number of protocols, this manual conversion is time-consuming and error-prone. The same applies for the other imaging devices noted above.

SUMMARY OF THE INVENTION

An object of the invention is to provide a method to configure an imaging device that reduces the time, cost and/or the tendency toward error in the conversion of protocols for the operation of a new imaging device.

According to the invention this object is achieved by providing a database that contains variants of protocols for the operation of imaging devices that contain parameter values for parameters. Furthermore, the database contains types of imaging devices that include attributes that describe predetermined properties of the imaging devices. The database for each variant contains an association of the imaging device type for which the respective variant was developed.

In a training phase, a computer executes a data-driven learning procedure (neural network) and thereby determines relationships between the parameters among one another and/or between the parameters and the associated types that it stores as a pattern in a knowledge base. In an application phase, the computer later determines a protocol plan for an operation of an imaging device with a target type using the determined pattern.

The invention also encompasses a non-transitory computer-readable storage medium encoded with computer program (programming instructions) that causes the method to be executed in the previously described computer. The invention also comprises the computer itself which is programmed in order to execute the method.

The method offers the advantage that the automatic conversion of the protocols is improved so that less manual post-processing is required. With the use of the pattern from the knowledge base the computer creates a protocol plan whose parameter values are closer to an optimum than parameter values which are calculated with known conversion software. The efficiency and quality of the conversion is thus improved. Given a sufficiently large quantity of data, the data-driven learning method enables individual variations in the existing protocols which are caused by different preferences of the experts which have created these. The relationships between the parameters among one another and/or between the parameters and the associated types can be determined in this manner.

The improved quality of the protocol plan reduces the cost of a manual post-processing. Work time and costs to convert the protocols for new types of imaging devices are reduced. Furthermore, a higher consistency of the protocols among one another is achieved both between product families and between individual configurations. Finally, the quality of the protocols is improved overall.

BRIEF DESCRIPTION OF THE DRAWINGS

FIG. 1 shows a user interface with protocol categories and protocols.

FIG. 2 illustrates a simple method to configure an imaging device.

FIG. 3 illustrates an improved method to configure an imaging device in accordance with the invention.

FIG. 4 illustrates protocols for different types of imaging devices

DESCRIPTION OF THE PREFERRED EMBODIMENTS

Figure 5:
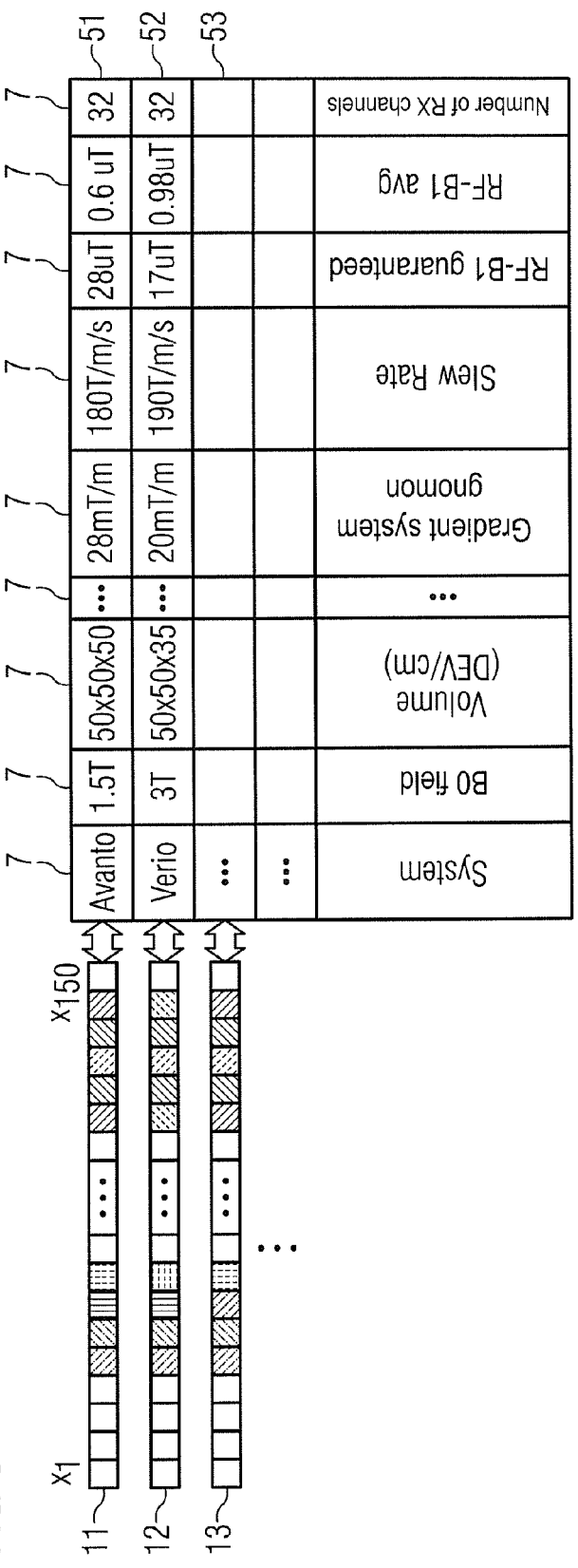
FIG. 5 illustrates a data-driven learning method to determine relationships between parameters and/or types of imaging devices in accordance with the invention.

Among other things, the following exemplary embodiments refer to magnetic resonance tomography and the respective protocols necessary therefor. However, the invention is not limited to magnetic resonance tomography; but can be applied to arbitrarily different imaging devices that must be configured by protocols.

FIG. 1 shows a user interface 10 as is known for processing of protocols to configure imaging devices. Protocol categories 1 in a tree structure are shown in a left portion of the user interface 10. In the right portion of the user interface 10, protocols 2 are shown which are contained in the protocol category 1 marked by an ellipse in the left portion. For example, the protocols 2 respectively define a sequence for image acquisition by a magnetic resonance tomograph whose duration is likewise indicated in FIG. 1.

FIG. 2 shows a simple method for configuration of an imaging device with a new type. A source parameter vector 3 is provided in a parameter space 6. The dimensions of the parameter space are, for example, 15-25 parameters which must be adapted to the new type of imaging device for each of the protocols 2 from FIG. 1. The source parameter vectors 3 contain the previous parameter values of the respective parameters from an existing protocol that should be converted into a new protocol.

An automatic conversion of the source parameter vector 3 into a plan parameter vector 4 is initially conducted automatically with the aid of a conversion software. The conversion software initially imports the source parameter vector 3 and checks whether the imported source parameter vector 3 is capable of running on the new type of imaging device. In the event that this is not the case, the plan parameter vector 4 is sought in the local neighborhood of the imported source parameter vector 3. However, since the plan parameter vector frequently does not deliver any satisfactory results, an expert subsequently determines step-by-step improvements (indicated by dots in FIG. 2) which the expert checks for their validity or capability of being executed on the new type of imaging device within the scope of an intended image acquisition sequence. The parameter space 6 does not need to be continuous since some regions may possibly not be allowed for the parameter vectors. It is also possible that nonlinear dependencies exist between the parameters. As shown in FIG. 2, the expert therefore only arrives at a target parameter vector 5 which has optimal properties for the operation of the imaging device after detours and numerous attempts.

FIG. 3 shows an improved method for configuration of an imaging device with a new type. As is shown in FIG. 2, a parameter space 6, a source parameter vector 3, a plan parameter vector 4 and a target parameter vector 5. However, the plan parameter vector 4 which is calculated by the improved method already lies much closer to the optimal target parameter vector 5, so the time cost for an expert is significantly reduced.

The final modification of the plan parameter vector 4 (shown in FIG. 3) relative to the target parameter vector 5 can be performed by the expert, but also by a conversion software. This hereby checks the plan parameter vector 4 with regard to a basic image acquisition sequence which the imaging device should execute, and correspondingly modifies the plan parameter vector 4 so that it can be executed by the imaging device as a target parameter vector 5 in the course of the image acquisition sequence.

The improved calculation of the plan parameter vector 4 is based on a data-driven learning algorithm or procedure, such as is implemented by a neural network, which provides knowledge about dependencies between parameters among one another and/or types of imaging devices. For example, a statistical learning procedure which contains a cluster analysis and a factor analysis is suitable as a data-driven learning procedure.

The following table shows two variants of a protocol which are tailored to two different types of magnetic resonance tomographs that are respectively cited in the column title. The types differ in the gradient system (SQ or, respectively, Q). 10 parameters are shown that possess different values in the two variants of the protocol.

The data-driven learning method extracts typical variation patterns in the protocols that result via a different gradient system, for example. For example, a definite reduction after the protocol was converted from type 1 to type 2 can respectively be recognized in the table, for example for the parameters "phase oversampling", "phase resolution" and "bandwidth". Such relationships are extracted via the data-driven learning methods.

The data-driven learning method among other things implements an automatic clustering in order to determine both groups of parameters that contain typical variation patterns, and to determine groups of protocols in which these variation patterns occur.

| Parameter | Type 1 (SQ) | Type 2 (Q) |
| --- | --- | --- |
| Base resolution | 256 | 384 |
| Phase oversampling | 100% | 85% |
| FoV | 140 mm | 180 mm |
| Phase resolution | 100% | 87% |
| A >> P | 140 mm | 180 mm |
| F >> H | 140 mm | 180 mm |
| Bandwidth | 501 Hz/Px | 434 Hz/Px |
| TR | 4360 ms | 5120 ms |
| TE | 108.0 ms | 112.0 ms |
| Echo interval | 7.7 ms | 8.58 ms |

In the following reference is made both to FIG. 4 and FIG. 5.

FIG. 4 shows a first variant 11, a second variant 12 and a third variant 13 of a protocol which contains 150 parameters. Each variant accordingly contains 150 parameter values $x_1 \ldots x_{150}$ that form a parameter vector x. The variants have different parameter values $x_1 \ldots x_{150}$ which are indicated by different shadings of the respective boxes. The first variant 11 contains parameter values $x_1 \ldots x_{150}$ which are optimized for a first type 51 (shown in FIG. 5) of an imaging device. The second variant 12 contains parameter values $x_1 \ldots x_{150}$ which are optimized for a second type 52 of an imaging device. The third variant 13 correspondingly contains parameter values $x_1 \ldots x_{150}$ which are optimized for a third type 53.

In the course of a search 21, in the first variant 11, the second variant 12 and the third variant 13 a first segment 31 and a second segment 32 are identified that, for example, have similar parameter values in the individual variants. This is to be understood only as an example since an arbitrary number of such segments can be determined in the course of the search 21. A machine learning method ascribes differences of the parameter values between the variants to differences of the associated types of the imaging devices. For example, statistical correlations or expert knowledge which can be provided by rules or functions are used for this. The differences can also be ascribed to a dependency 40 which exists between different parameters. The goal is thus to extract knowledge about relationships between the parameters among one another or between the parameters and the types automatically from the large data set of existing protocols.

FIG. 5 shows a data-driven learning method to determine relationships between parameters and types of imaging devices. As in FIG. 4, the first variant 11, the second variant 12 and the third variant 13 are shown with its individual parameter values $x_1 \ldots x_{150}$ which are respectively tailored to the first type 51, the second type 52 and the third type 53 of imaging device. The first type 51, the second type 52 and the third type 53 hereby respectively consist of attributes 7 which define technical characteristics of the respective imaging device. Each type is typically defined by 10-25 protocol-relevant attributes 7, of which only a selection is shown in FIG. 5. The data-driven learning method is aimed towards determining relationships between the parameters and the types. For example, a probabilistic model P(x|y) is determined for this. Which parameter vector x is most probable when a type y is predetermined is thereby examined.

Figure 6:
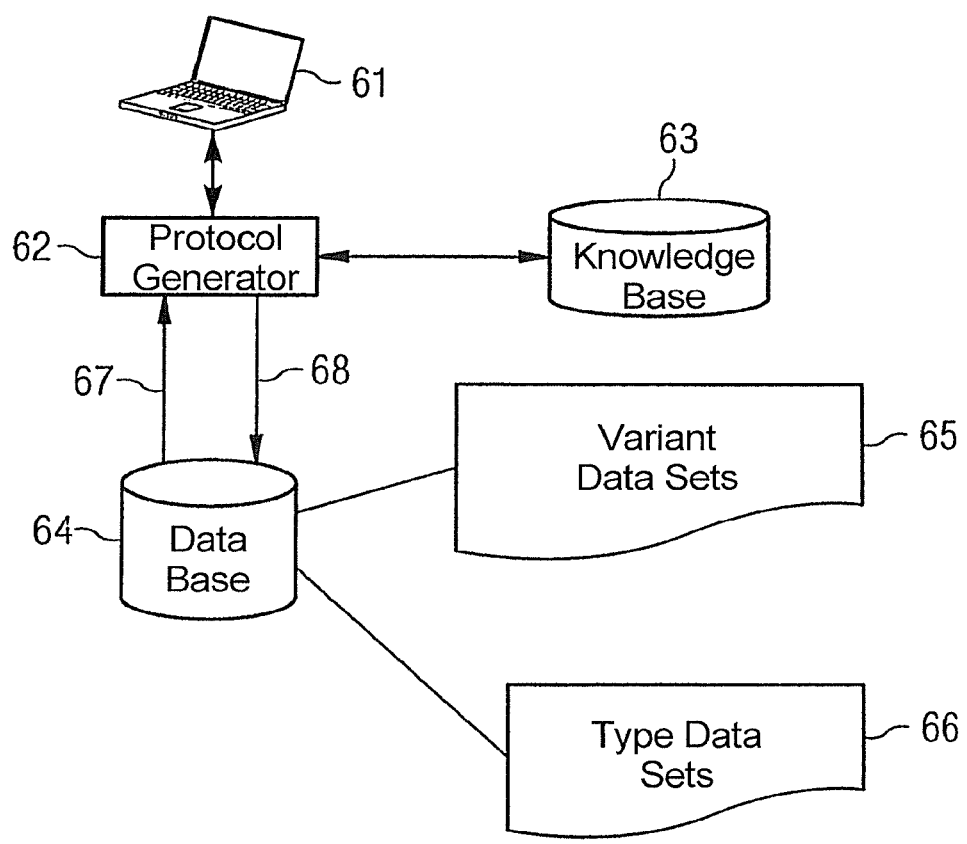
FIG. 6 is a system architecture for execution of the method in accordance with the invention.

FIG. 6 shows a system architecture for execution of the method. With the use of a computer 61, an expert initially selects an existing type of imaging device or adds a new one. This type is designated as a target type in the following. The expert subsequently selects which protocols should be adapted. The computer 61 now identifies portions of the protocols which must be changed and proposes new parameter values. For this, with a read access 67 the computer 61 retrieves existing protocols from a database 64 in the form of variant data sets 65 as well as known types of imaging devices in the form of type data sets 66.

The variant data sets 65 contain an identifier for an associated type of imaging device, a protocol identifier for a respective protocol, as well as a parameter identifier and a parameter value for each parameter. For example, each variant data set 65 can include 150 parameter values, of which approximately 25 must be considered. Approximately 1500-1800 variant data sets 65 are typically stored in the database 64 for each type of an imaging device.

Each type data set 66 contains an identifier for a type of imaging device, as well as a system description which consists of 15-25 attributes, for example.

A protocol generator 62 enables the computer 61 to suggest new parameter values for the target type established by the expert. For this purpose, the protocol generator 62 accesses a knowledge base 63 that contains knowledge regarding the conversion of parameter values, for example in the form of correlations between parameters and system characteristics, rules or probabilistic models. By means of known methods of case-based reasoning, from the present variant data sets 65 and from the information of the knowledge base 63 the protocol generator 62 can suggest a protocol plan with new parameter values for the target type established by the expert. The knowledge base 63 can be a separate database that, however, can also be contained in the database 64 or be identical to this. The protocol generator 62 is finally set up in order to store the new parameter values for the target type as a variant data set 65 in the database 64 with a write access 68. If the parameter values which the protocol generator 62 suggests have still not been checked by this as to whether they are valid for an intended image acquisition sequence, this check takes place via a conversion software in a downstream step.

Figure 7:
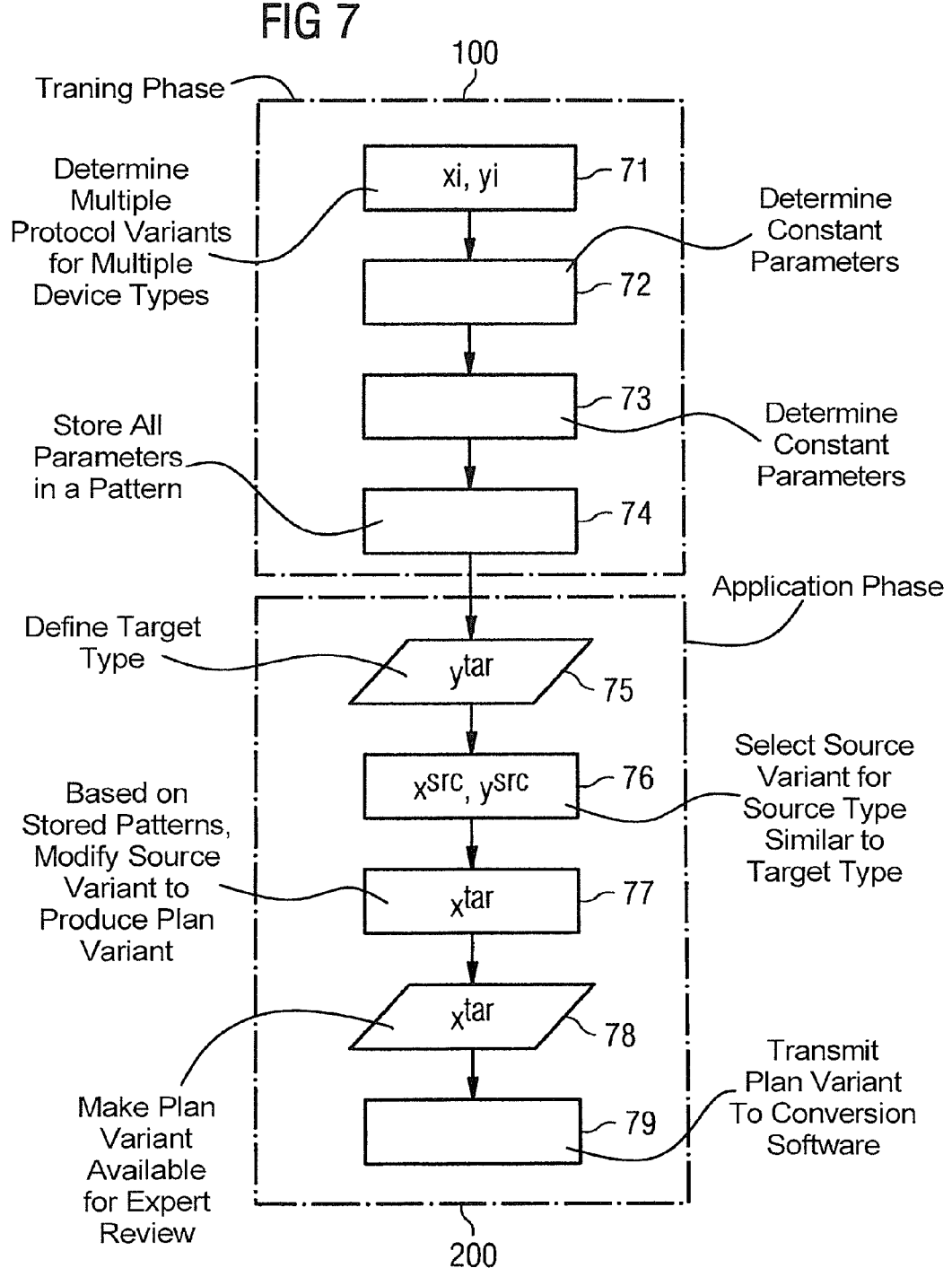
FIG. 7 is a flowchart of an embodiment of the method in accordance with the invention.

In the following a preferred exemplary embodiment of the invention is described in detail, wherein both FIG. 6 and FIG. 7 are referenced.

In an extension of FIG. 6, FIG. 7 shows a program workflow plan for a possible implementation of the method. The method begins with a training phase 100 which is followed by an application phase 200. As described in FIG. 6, variants $x_i$ of protocols are stored in the database 64 in the form of variant data sets 65 for an operation of imaging devices, which variant data sets 65 contain parameter values for parameters. Furthermore, types $y_i$ of imaging devices in the form of type data sets 66 (which consist of attributes 7 that describe predetermined properties of the imaging devices) are stored in the database 64. Moreover, for which type $y_i$ the respective variant $x_i$ was developed is stored for each variant $x_i$ in the database 64. An association according to which a variant $x_i$ of an imaging device is associated with type $y_i$ thus results. It does not necessarily need to be a 1:1 association. It is likewise possible that one and the same variant $x_i$ is associated with multiple types $y_i$, for example, in the event that these should be controlled according to the same protocol workflow.

A microprocessor of the computer 61 is programmed in order to determine relationships between the parameters of the variants $x_i$ among one another and/or between the parameters and the associated types $y_i$ via a data-driven learning procedure in the training phase, and to store these as a pattern in the knowledge base 63.

For this purpose, the following steps are implemented for at least one protocol. All variants $x_i$ of the protocol are initially determined in that the respective variant data sets 65 are retrieved from the database 64. Since different variant data sets 65 exist for different types $y_i$, in this first Step 71, multiple variants $x_i$ of the protocol are normally determined for a plurality of types $y_i$ in this first Step 71. For example, a vector whose elements contain the individual parameter values of this variant $x_i$ and in which the variable i indicates a sequential number of the variant of the respective protocol is suitable as a data format of the variant $x_i$. A vector whose elements consist of values for the attributes of the type $y_i$ is correspondingly suitable as a data format for the type $y_i$. The common i indicates that the type $y_i$ is associated with the variant $x_i$, for example in that the type $y_i$ is referenced in the variant data set 65 of the variant $x_i$. A set $V=\{(x_i, y_i)|i=1, \ldots, n\}$ results from this which contains all variants $x_i$ of the considered protocol in connection with the associated types $y_i$.

Constant parameters whose parameter values are constant in the variants $x_1$ of the protocol under predetermined boundary conditions are now determined in a second Step 72. For example, parameter values for resolution and matrix can be constant in all variants $x_i$ when a value for an attribute 7 with the title "$B_0$ field" is at "3T" in the associated types $y_i$, for example. Naturally, additional boundary conditions can also be taken into account.

In a third Step 73, variable parameters are determined whose parameter values vary in the variants $x_i$ by a periodic factor in the variants $x_i$. For example, in this third Step 73 it is determined that the parameter values of the parameters TR and TE in a variant x3 are reduced by a specific factor to parameter values for a variant $x_4$.

Alternatively, in a third Step 73 variable parameters are determined whose parameter values in the variants $x_i$ vary by a factor depending on a modification of an attribute of the associated types $y_i$. This second case differs in that here it is incorporated into the variable parameters that the change of the parameter values correlates with a change of attributes of the types associated with this. How the values of attributes of associated types $y_3$ and $y_4$ vary is thus taken into account, wherein the cited variants and types form tuples $(x_3, y_3)$ and $(x_4, y_4)$. For example, it is determined that the parameters "bandwidth" and "phase resolution" respectively change by a specific factor and/or the relationship of these parameters to one another varied given a defined change of the gradient system. In the first case, the variable parameters are thus determined under exclusive consideration of the parameters themselves; in contrast to this, in the second case the variable parameters are determined with incorporation of the associated types.

Correlated parameters whose parameter values correlate with one another in the variants $x_i$ can be determined in an additional step that is optional and not explicitly shown in FIG. 7.

Finally, the constant parameters and their parameter values, the variable parameters and their factors as well as the correlated parameters are stored in a pattern for the training phase 100 of the data-driven learning method. This takes place in a fourth Step 74. Individual cited steps can also be omitted beforehand, such that only constant parameters, variable parameters or correlated parameters are stored in the pattern, for example.

As a result, the patterns contain factors in order to vary the parameter values of selected parameters in the database 64, as well as parameter groups which respectively consist of at least two parameters whose parameter values vary only jointly in the database or whose values are correlated with one another.

As described above, the patterns are respectively determined separately for individual protocols in that variants of the respective protocol were checked for different types $y_i$. In a development of the present exemplary embodiment, a significant portion of the data-driven learning method exists in analyzing these patterns across different protocols in the third Step 73 and assembling these into more general patterns. The statistical evaluation that is necessary for this is abetted by the typically large number of protocols.

For instance, commonalities in protocols in which the parameter "phase resolution" was increased given a specific change of the gradient system can be sought by means of known methods of cluster analysis. The result exists in a pattern that characterizes the commonalities of the protocols, the parameter changes and the associated types $y_i$.

For example, such a pattern could contain the following information: given a change from a first type $y_1$ to a second type $y_2$, the parameter "phase resolution" increases by 10 percent in protocols which satisfy predetermined boundary conditions (for example a categorization with "T1" and a defined sequence for image acquisition for the head of a patient); the parameters "phase oversampling" and "bandwidth" are simultaneously varied by specific factors.

The previously determined (and possibly assembled) patterns are stored in the knowledge base 63 in the fourth Step 74. Additional limitations, boundary conditions and rules can hereby be added manually by an expert if necessary, for example concerning aspects which are not explicitly described in the protocols (for instance a time interval for which a patient should hold his breath during an image acquisition of his abdominal region).

The application phase 200 begins with a definition of a target type $y^{tar}$ by an expert in a fifth Step 75. The attributes of the target type $y^{tar}$ hereby described technical properties of a new imaging device that should be configured. In the application phase 200, a protocol plan for the operation of the new imaging device with the target type $y^{tar}$ is determined using the determined pattern.

In addition to the specification of the attributes of the target type $y^{tar}$, in the fifth Step 75 the expert can also establish which protocols should be converted for the target type $y^{tar}$.

The conversion of an individual protocol is described in the following. For this, in a sixth Step 76 the protocol generator 62 selects from the database 64 a source variant $x^{src}$ which belongs to a source type $y^{src}$ that is optimally similar to the target type $y^{tar}$. The tuple $(x^{src}, y^{src})$ at which $y^{src}$ and $y^{tar}$ have the greatest similarity to one another is thus retrieved from the database 64.

Based on the previously stored patterns or additional limitations and rules that are stored in the knowledge base 63, in a seventh Step 77, the protocol generator 62 modifies the source variant $x^{src}$ and thus determines a plan variant $x^{tar}$ for the protocol to be converted. For this purpose, all patterns which satisfy the predetermined boundary conditions are retrieved from the knowledge base 63 and are successively applied to the tuple $(x^{src}, y^{src})$. For this purpose, the corresponding patterns can be prioritized, for example in that specific patterns which have more conditions than more general patterns are treated with priority. Insofar as necessary, parameter values can be interpolated or extrapolated, for which regression methods—for instance a non-linear local regression—are suitable. The source variant $x^{src}$ is thus recalculated into a plan variant $x^{tar}$ for the target type $y^{tar}$ using the pattern stored in the knowledge base 63.

In an eighth step 78, the plan variant $x^{tar}$ is output to the expert (for example via a monitor), which expert can modify this insofar as the expert desires.

In a ninth Step 79 the plan variant $x^{tar}$ is finally transmitted to a conversion software that checks this software with regard to its ability to run within the scope of an intended image acquisition sequence and makes final modifications in order to ensure that the final parameter values are capable or running on the imaging device with the target type $y^{tar}$. The protocol plan for the operation of the imaging device with the target type $y^{tar}$ now exists with the final version of the plan variant $x^{tar}$.

In a second scenario, instead of the plan variant $x^{tar}$ only one guideline for each protocol is also created by the protocol generator 62 and transferred to the conversion software. This guideline then controls the conversion which the conversion software implements. The guideline contains information with regard to the meaning of individual parameters, the order in which parameters should be converted, dependencies between parameters and preferred value ranges of parameters. Since the guideline is created individually for each protocol by the protocol generator 62, it can be designed both specific to the protocol and specific to the type. It thus replaces the rigid scheme of a simple conversion software which implements only a local neighborhood search in the conversion. In this second scenario, the protocol plan thus contains rules according to which parameter rules are to be selected for the operation of the imaging device with the target type $y^{tar}$.

According to a further exemplary embodiment that is a variant of the previously described exemplary embodiments, the data-driven learning procedure extracts knowledge by comparing at least two variants $x_i$ of a protocol with one another. No information with regard to the associated types $y_i$ and their attributes are required. Instead of this, typical changes of parameter values between the variants $x_i$ are determined without setting these in relation to the respectively types $y_i$ and their attributes. For example, the following is then stored in the patterns:

parameter values for a parameter "echo interval" are typically changed with a defined factor, there are parameter groups whose parameter values are in principle changed in common in a specific context, for example in protocols for an image acquisition of the head region of the person, a relationship between two parameter values is always modified by a similar factor, etc.

This exemplary embodiment is suitable for assistance in a conversion of client protocols in system updates. In that a customer version of a protocol is compared with the original version of the same protocol, modification patterns can be determined which reflect the business model of the customer. For example, a customer can place a focus on image quality or on short acquisition time in his protocols. After the corresponding patterns have been extracted, these can be used in order to adapt new protocols corresponding to the business model of the customer.

The described exemplary embodiments can be freely combined with one another.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to configure an imaging device comprising:
   in an electronic database, storing a plurality of different variants of respective protocols for operating medical image data acquisition devices in order to acquire medical image data from a patient, each stored protocol variant containing parameter values for parameters to implement image data acquisition from the patient according to the respective variant;
   also in said electronic database, storing a plurality of different types of medical image data acquisition devices by, for each of said types of medical image data acquisition devices, storing attributes that describe predetermined properties of the respective types of medical image data acquisition devices;
   in said electronic database, for each of said protocol variants, storing an association for each type of medical image data acquisition device for which the respective protocol variant was developed;
   from a computer, accessing said database and, in said computer, executing a training phase of a learning procedure using said protocol variants, said types of medical image data acquisition devices, and said associations stored in said database and, in said training phase, determining respective relationships between respective parameters of the protocol variants and respective associated types of medical image data acquisition devices, and storing said relationships as a pattern in a knowledge base for said learning procedure; and
   providing an input to said computer that designates, as a designated medical image data acquisition device, a medical image data acquisition device that is not one of said types of medical image data acquisition devices and, in said computer, implementing an application phase of said learning procedure and, in said application phase, automatically generating a protocol plan for operating said designated medical image data acquisition device using the pattern stored in said knowledge base, said protocol plan being selected from the group consisting of a protocol plan containing a plan variant with parameter values for operating said designated medical image data acquisition device, and a protocol plan containing rules according to which parameter values are selected for operating said designated medical image data acquisition device, and making said protocol plan available at an output of the computer.

2. A method as claimed in claim 1 comprising, in said training phase executed by said computer:
   generating said pattern to contain factors for varying at least some of said parameter values in said database; and
   generating said pattern to contain parameter groups that respectively consist of two parameters having parameter values in said database that vary jointly with each other or are correlated with each other.

3. A method as claimed in claim 1 comprising executing, as said learning procedure in said computer, a statistical learning procedure that implements a cluster analysis.

4. A method as claimed in claim 1 comprising executing said learning procedure in said computer for at least one protocol, by:
   learning variants of said at least one protocol from said electronic database;
   determining constant parameters, having parameter values in said variants of said at least one protocol that are constant under predetermined boundary conditions;
   determining variable parameters having parameter values that vary as a periodic factor in said variants of said at least one protocol;
   determining correlated parameters having respective parameter values that are correlated with each other in the variants of said at least one protocol; and
   storing, in a pattern for said at least one of said protocols, the constant parameters and their respective parameters values and the variable parameters and their respective factors, and said correlated parameters.

5. A method as claimed in claim 1 comprising executing said learning procedure in said computer for at least one protocol, by:
   learning all variants of said at least one protocol from said electronic database;
   determining variable parameters having parameter values in said variants of said at least one protocol that vary by a factor dependent on a modification of at least one of said attributes of a type of medical image data acquisition device associated in the database with the variants of said at least one protocol; and
   storing said variable parameters and their respective factors, and the associated attributes of said types in one of said patterns in said knowledge base.

6. A method as claimed in claim 5 comprising also executing said learning procedure in said computer for said at least one protocol, by:
   comparing respective patterns in said knowledge base for different protocols, to obtain a comparison result; and
   using said comparison result to assemble selected patterns in said knowledge base into a more general pattern.

7. A method as claimed in claim 1 comprising:
   establishing said attributes of each target type in said application phase;
   from said electronic database, selecting, via said computer, a source variant that is associated with a source type of medical image data acquisition device that is similar to the type of medical image data acquisition device of said designated medical image data acquisition device; and
   in said computer, recalculating said source variant into a plan variant for the type of medical image data acquisition device of said designated medical image data acquisition device, using the pattern stored in the knowledge base.

8. A non-transitory computer-readable storage medium encoded with programming instructions, said storage medium being loaded into a computer having access to a database that contains variants of respective protocols for operating medical image data acquisition devices in order to acquire medical image data from a patient, said variants and protocols containing parameter values for parameters that operate the medical image data acquisition devices to implement image data acquisition from the patient according to the respective variant, and that also contains respective types of medical image data acquisition devices represented by attributes that describe predetermined properties of the respective types of medical image data acquisition devices, and that contains, for each of said variants, an association of that variant for a type of medical image data acquisition device for which that variant was developed, said programming instructions causing said computer to:

- access said database and execute a training phase of a learning procedure using said variants, said types and said associations stored in said database and, in said training phase, determining respective relationships between respective parameters and between respective parameters and respective associated types of medical image data acquisition devices, and storing said relationships as a pattern in a knowledge base for said learning procedure; and
- upon receiving an input that designates, as a designated medical image data acquisition device, a medical image data acquisition device that is not one of said types of medical image data acquisition devices, implement an application phase of said learning procedure and, in said application phase, automatically generate a protocol plan for operating said designated medical image data acquisition device using the pattern stored in said knowledge base, said protocol plan being selected from the group consisting of a protocol plan containing a plan variant with parameter values for operating said designated medical image data acquisition device, and a protocol plan containing rules according to which parameter values are selected for operating said designated medical image data acquisition device, and make said protocol plan available as an output.

9. A computerized system comprising:

an electronic database in which a plurality of different variants of respective protocols for operating an imaging device are stored medical image data acquisition devices in order to acquire medical image data from a patient, each stored variant containing parameter values for parameters to implement image data acquisition from the patient according to the respective variant;

said electronic database also having stored therein a plurality of different types of medical image data acquisition devices in a storage format comprising, for each of said types of medical image data acquisition devices, storing attributes that describe predetermined properties of the respective types of medical image data acquisition devices;

said electronic database also having stored therein, for each of said variants, an association for each type of medical image data acquisition device for which the respective variant was developed;

a computer configured to access said database and execute a training phase of a learning procedure using said variants, said types and said associations stored in said database and, in said training phase, determine respective relationships between respective parameters and between respective parameters and respective associated types of medical image data acquisition devices, and store said relationships as a pattern in a knowledge base for said learning procedure; and said computer being configured to receive an input that designates, as a designated medical image data acquisition device, a medical image data acquisition device that is not one of said types of medical image data acquisition devices, and in response to said input said computer being configured to implement an application phase of said learning procedure and, in said application phase, automatically determine generate a protocol plan for operating said designated medical image data acquisition device using the pattern stored in said knowledge base, said protocol plan being selected from the group consisting of a protocol plan containing a plan variant with parameter values for operating said designated medical image data acquisition device, and a protocol plan containing rules according to which parameter values are selected for operating said designated medical image data acquisition device, and to make said protocol plan available at an output of the computer.

\* \* \* \* \*